(12) United States Patent
Diehnelt et al.

(10) Patent No.: US 10,125,167 B2
(45) Date of Patent: Nov. 13, 2018

(54) COMPOSITIONS AND METHODS FOR TREATING MRSA INFECTIONS AND FOR SENSITIZING MRSA TO BETA-LACTAM ANTIBIOTICS

(71) Applicant: Arizona Board of Regents on behalf of Arizona State University, Scottsdale, AZ (US)

(72) Inventors: Chris Diehnelt, Chandler, AZ (US); Stephen Johnston, Tempe, AZ (US); Pamela Hall, Alburquerque, NM (US)

(73) Assignee: ARIZONA BOARD OF REGENTS ON BEHALF OF ARIZONA STATE UNIVERSITY, Scottsdale, AR (US)

( * ) Notice: Subject to any disclaimer, the term of this patent is extended or adjusted under 35 U.S.C. 154(b) by 0 days.

(21) Appl. No.: 15/368,178

(22) Filed: Dec. 2, 2016

(65) Prior Publication Data
US 2017/0158736 A1 Jun. 8, 2017

Related U.S. Application Data

(60) Provisional application No. 62/263,168, filed on Dec. 4, 2015.

(51) Int. Cl.
| | |
|---|---|
| *C07K 7/06* | (2006.01) |
| *A61K 38/08* | (2006.01) |
| *A61K 31/43* | (2006.01) |
| *A61K 31/431* | (2006.01) |
| *C07K 7/08* | (2006.01) |
| *A61K 38/00* | (2006.01) |

(52) U.S. Cl.
CPC .............. *C07K 7/06* (2013.01); *A61K 31/43* (2013.01); *A61K 31/431* (2013.01); *A61K 38/08* (2013.01); *C07K 7/08* (2013.01); *A61K 38/00* (2013.01); *C07K 2318/00* (2013.01)

(58) Field of Classification Search
None
See application file for complete search history.

(56) References Cited

U.S. PATENT DOCUMENTS

| 9,309,298 B2 | 4/2016 | Johnston et al. |
| 9,757,472 B2 | 9/2017 | Diehnelt et al. |
| 2011/0136727 A1 | 6/2011 | Svarovsky |
| 2011/0143953 A1 | 6/2011 | Johnston et al. |
| 2012/0021967 A1 | 1/2012 | Johnston et al. |
| 2012/0065123 A1 | 3/2012 | Johnston et al. |
| 2014/0128280 A1 | 5/2014 | Johnston et al. |
| 2014/0221253 A1 | 8/2014 | Johnston et al. |
| 2016/0022832 A1 | 1/2016 | Diehnelt et al. |
| 2016/0207984 A1 | 7/2016 | Diehnelt et al. |

FOREIGN PATENT DOCUMENTS

| WO | 2010111299 A2 | 9/2010 |
| WO | 2011029008 A2 | 3/2011 |
| WO | 2013067160 A2 | 5/2013 |
| WO | 2014165240 A1 | 10/2014 |
| WO | WO2015/031268 | * 3/2015 |

OTHER PUBLICATIONS

World Health Organization, "Antimicrobial resistance: global report on surveillance 2014", World Health Organization Report, Apr. 2014, Geneva, Switzerland, 256 pages.
United States Patent and Trademark Office, Office Action, U.S. Appl. No. 14/808,984, dated Jan. 25, 2017, 10 pages.
Mahalakshmi, R. et al., "The Use of D-Amino Acids in Peptide Design", 2006, D-Amino Acids: A New Frontier in Amino Acid and Protein Research, Chapter 5.9, Nova Science Publishers, Inc., pp. 415-430.
United States Patent and Trademark Office, Notice of Allowance, U.S. Appl. No. 14/913,089, dated Mar. 8, 2018, 5 pages.
Alley, S. et al., "Contribution of Linker Stability to the Activities of Anticancer Immunoconjugates", Bioconjugate Chemistry, Mar. 2008, 19(3), pp. 759-765.
Boucher, H. et al., "10×'20 Progress—Development of New Drugs Active Against Gram-Negative Bacilli: An Update From the Infectious Diseases Society of America", Clinical Infectious Diseases, Jun. 2013 (available online Apr. 2013), 56(12), pp. 1685-1694.
Brogden, N. et al., "Will new generations of modified antimicrobial peptides improve their potential as pharmaceuticals?", International Journal of Antimicrobial Agents, Sep. 2011 (available online Jul. 2011), 38(3), pp. 217-225.
Cassone, M. et al., "Synergy among antibacterial peptides and between peptides and small-molecule antibiotics", Expert Review of Anti-Infective Therapy, Jun. 2010, 8(6), pp. 703-716.
Centers for Disease Control and Prevention, "Antibiotic resistance threats in the United States, 2013", U.S. Department of Health and Human Services, Apr. 2013, Atlanta, GA, U.S.A., 114 pages.
Centers for Disease Control and Prevention, "Public health dispatch: Outbreaks of community-associated methicillin-resistant *Staphylococcus aureus* skin infections—Los Angeles County, California, 2002-2003", Canada Communicable Disease Report, Jun. 2003, 29(12), pp. 110-112.
Diehnelt, C. et al., "Discovery of High-Affinity Protein Binding Ligands—Backwards", PLoS One, May 2010, 5(5), e10728, 10 pages, doi:10.1371/journal.pone.0010728.
Domenyuk, V. et al., "A technology for developing synbodies with antibacterial activity", PLoS One, Jan. 2013, 8(1), e54162, 11 pages, https://doi.org/10.1371/journal.pone.0054162.
Farha, M. et al., "Collapsing the proton motive force to identify synergistic combinations against *Staphylococcus aureus*", Chemistry & Biology, Sep. 2013 (available online Aug. 2013), 20(9), pp. 1168-1178.

(Continued)

Primary Examiner — Karlheinz R. Skowronek
Assistant Examiner — Ronald T Niebauer
(74) Attorney, Agent, or Firm — Quarles & Brady LLP (57) ABSTRACT

Provided herein are compounds and compositions having antibiotic activity against methicillin resistant *Staphylococcus aureus* (MRSA). In particular, provided herein is a synbody that bactericidal against multiple strains of MRSA and that can be used in conjugation with currently approved β-lactam antibiotics to treat MRSA strains having resistance to β-lactam treatment. Also provided are methods of using the compounds and compositions for treating, preventing or reducing MRSA infections.

10 Claims, 5 Drawing Sheets

Specification includes a Sequence Listing.

(56) References Cited

OTHER PUBLICATIONS

Giuliani, A. et al., "Beyond natural antimicrobial peptides: multimeric peptides and other peptidomimetic approaches", Cellular and Molecular Life Sciences, Jul. 2011 (available online May 2011), 68(13), pp. 2255-2266.

Guo, L. et al., "Precision-guided antimicrobial peptide as a targeted modulator of human microbial ecology", PNAS USA, Jun. 2015, 112(24), pp. 7569-7574.

Gupta, N. et al., "Engineering a synthetic ligand for tumor necrosis factor-alpha", Bioconjugate Chemistry, Aug. 2011 (available Jul. 2011), 22(8), pp. 1473-1478.

Gupta, N. et al., "Whole-Virus Screening to Develop Synbodies for the Influenza Virus", Bioconjugate Chemistry, Sep. 2016, 27(10), pp. 2505-2512.

Hall, P. et al., "Nox2 modification of LDL is essential for optimal apolipoprotein B-mediated control of agr type III Staphylococcus aureus quorum-sensing", PLoS Pathogens, Feb. 2013, 9(2), e1003166, 16 pages, https://doi.org/10.1371/journal.ppat.1003166.

Haney, E et al., "Antimicrobial Peptides: An Introduction", Antimicrobial Peptides: Methods and Protocols (ed. Hansen, P.R.), 2017 (available online Dec. 2016), pp. 3-22, Springer, New York, USA.

He, J. et al., "Design and activity of a 'dual-targeted' antimicrobial peptide", International Journal of Antimicrobial Agents, Jun. 2009 (available online Feb. 2009), 33(6), pp. 532-537.

Hernandez-Gordillo, V. et al., "Dimeric unnatural polyproline-rich peptides with enhanced antibacterial activity", Bioorganic & Medicinal Chemistry Letters, Jan. 2014 (available Dec. 2013), 24(2), pp. 556-559.

Hughes, A. et al., "Immunosignaturing Can Detect Products from Molecular Markers in Brain Cancer", PLoS One, Jul. 2012,7(7), e40201, 7 pages, https://doi.org/10.1371/journal.pone.0040201.

Kaneti, G. et al., "Simultaneous breakdown of multiple antibiotic resistance mechanisms in S. aureus", The FASEB Journal, Dec. 2013 (available online Aug. 2013), 27(12), pp. 4834-4843.

Koh, J. et al., "N-Lipidated Peptide Dimers: Effective Antibacterial Agents against Gram-Negative Pathogens through Lipopolysaccharide Permeabilization", Journal of Medicinal Chemistry, Aug. 2015 (available online Jul. 2015), 58(16), 6533-6548.

Lainson, J. et al., "Conjugation Approach to Produce a Staphylococcus aureus Synbody with Activity in Serum", Bioconjugate Chemistry, Oct. 2015 (available online Sep. 2015), 26(10), pp. 2125-2132.

Lainson, J. et al., "Synthetic Antibacterial Peptide Exhibits Synergy with Oxacillin against MRSA", ACS Medicinal Chemistry Letters, Jul. 2017, 8(8), pp. 853-857.

Lee, B. et al., "Targeting antimicrobial-resistant bacterial respiratory tract pathogens: it is time to 'get smart'", Current Opinion in Pulmonary Medicine, May 2015, 21(3), pp. 293-303.

Lehar, S. et al., "Novel antibody—antibiotic conjugate eliminates intracellular S. aureus", Nature, Nov. 2015, 527 (7578), pp. 323-328.

Lewis, K., "Platforms for antibiotic discovery", Nature Reviews Drug Discovery, May 2013 (available online Apr. 2013), 12(5), pp. 371-387.

Li, H. et al., "Roles of d-Amino Acids on the Bioactivity of Host Defense Peptides", International Journal of Molecular Sciences, Jul. 2016 (available online Jun. 2016), 17(7), article 1023, 27 pages, doi:10.3390/ijms17071023.

Li, Z. et al., "Hp1404, a new antimicrobial peptide from the scorpion Heterometrus petersii", PLoS One, May 2014, 9 (5), e97539, 9 pages, https://doi.org/10.1371/journal.pone.0097539.

Lichtenecker, R, et al., "Iterative Antimicrobial Candidate Selection from Informed D-/L-Peptide Dimer Libraries", ChemBioChem, Dec. 2013 (available online Oct. 2013), 14(18), pp. 2492-2499.

Liu, S. et al., "Multivalent Antimicrobial Peptides as Therapeutics: Design Principles and Structural Diversities", International Journal of Peptide Research and Therapeutics, Sep. 2010 (available online Aug. 2010), 16(3), pp. 199-213.

Lu, X. et al., "In Vitro Activity of Sodium New Houttuyfonate Alone and in Combination with Oxacillin or Netilmicin against Methicillin-Resistant Staphylococcus aureus", PLoS One, Jul. 2013, 8(7), e68053, 8 pages, https://doi.org/10.1371/journal.pone.0068053.

Mann, P. et al., "Murgocil is a highly bioactive staphylococcal-specific inhibitor of the peptidoglycan glycosyltransferase enzyme MurG", ACS Chemical Biology, Nov. 2013 (available online Aug. 2013), 8(11), pp. 2442-2451.

Marks, L. et al., "Sensitization of Staphylococcus aureus to methicillin and other antibiotics in vitro and in vivo in the presence of HAMLET", PLoS One, May 2013, 8(5), e63158, 11 pages, https://doi.org/10.1371/journal.pone.0063158.

Maxson, T. et al., "Targeted Treatment for Bacterial Infections: Prospects for Pathogen-Specific Antibiotics Coupled with Rapid Diagnostics", Tetrahedron, Jun. 2016 (available online Oct. 2015), 72(25), pp. 3609-3624.

Mercer, D. et al., "Peptides as the next generation of anti-infectives", Future Medicinal Chemistry, Mar. 2013, 5(3), pp. 315-338.

Molina, K. et al., "Resistance to Non-glycopeptide Agents in Serious Staphylococcus aureus Infections", Current Infectious Disease Reports, Dec. 2016 (available online Nov. 2016), 18(12), article 47, 6 pages, https://doi.org/10.1007/s11908-016-0553-6.

Morales Betanzos, C. et al., "Bacterial glycoprofiling by using random sequence peptide microarrays", ChemBioChem, Mar. 2009 (available online Feb. 2009), 10(5), pp. 877-888.

Muller, A. et al., "Daptomycin inhibits cell envelope synthesis by interfering with fluid membrane microdomains", PNAS USA, Oct. 2016, 113(45), E7077-E7086.

Patent Cooperation Treaty, International Bureau, International Preliminary Report on Patentability for PCT/US2012/063029, 10 pages, dated May 6, 2014.

Patent Cooperation Treaty, International Searching Authority, International Search Report for PCT/US2012/063029, 8 pages, dated May 24, 2013.

Patent Cooperation Treaty, International Searching Authority, Written Opinion for PCT/US2012/063029, 9 pages, dated May 5, 2014.

Peacock, S. et al., "Mechanisms of Methicillin Resistance in Staphylococcus aureus", Annual Review of Biochemistry, Jun. 2015, 84, pp. 577-601.

Podoll, J., et al., "Bio-inspired synthesis yields a tricyclic indoline that selectively resensitizes methicillin-resistant Staphylococcus aureus (MRSA) to (β-lactam antibiotics", PNAS USA, Sep. 2013, 110(39), pp. 15573-15578.

Rothfork, J. et al., "Fibrinogen depletion attenuates Staphyloccocus aureus infection by preventing density-dependent virulence gene up-regulation", The Journal of Immunology, Nov. 2003, 171(10), pp. 5389-5395.

Rothfork, J. et al., "Inactivation of a bacterial virulence pheromone by phagocyte-derived oxidants: new role for the NADPH oxidase in host defense", PNAS USA, Sep. 2004, 101(38), pp. 13867-13872.

Sarig, H. et al., "A miniature mimic of host defense peptides with systemic antibacterial efficacy", The FASEB Journal, Jun. 2010 (available online Feb. 2010), 24(6), pp. 1904-1913.

Sully, E. et al., "Selective chemical inhibition of agr quorum sensing in Staphylococcus aureus promotes host defense with minimal impact on resistance", PLoS Pathogens, Jun. 2014, 10(6), e1004174, 14 pages, https://doi.org/10.1371/journal.ppat.1004174.

Svarovsky, S. et al., "High-Throughput Platform for Rapid Deployment of Antimicrobial Agents", ACS Combinational Science, Nov. 2011 (available online Sep. 2011), 13(6), pp. 634-638.

Wang, G. et al., "APD3: the antimicrobial peptide database as a tool for research and education", Nucleic Acids Research, Jan. 2016 (available online Nov. 2015), 44(D1), pp. D1087-D1093.

Wang, H. et al', "Discovery of wall teichoic acid inhibitors as potential anti-MRSA β-lactam combination agents", Chemistry & Biology, Feb. 2013, 20(2), pp. 272-284.

(56) References Cited

OTHER PUBLICATIONS

Williams, B. et al., "Creating Protein Affinity Reagents by Combining Peptide Ligands on Synthetic DNA Scaffolds", Journal of the American Chemical Society, Dec. 2009 (available online Nov. 2009), 131(47), pp. 17233-17241.

* cited by examiner

COMPOSITIONS AND METHODS FOR TREATING MRSA INFECTIONS AND FOR SENSITIZING MRSA TO BETA-LACTAM ANTIBIOTICS

CROSS-REFERENCE TO RELATED APPLICATIONS

This application claims priority to U.S. Provisional Application No. 62/263,168, filed Dec. 4, 2015, which is incorporated by reference herein as if set forth in its entirety.

STATEMENT AS TO RIGHTS TO INVENTIONS MADE UNDER FEDERALLY SPONSORED RESEARCH AND DEVELOPMENT

This invention was made with government support under W911NF-10-1-0299 awarded by the Army Research Office. The government has certain rights in the invention.

BACKGROUND

Antibiotic resistance is a global crisis with few solutions on the horizon [1]. In the United States, resistant infections account for over 2,000,000 illnesses each year with methicillin-resistant *Staphylococcus aureus* (MRSA) responsible for over 11,000 deaths per year [2]. Despite the severity of the problem, there are few new molecules nearing approval [3] illustrating the need for new antibiotic discovery platforms [4].

Antimicrobial peptides (AMPs) have often been proposed as new antibiotics and many are in clinical development [5]. While the in vivo behavior of AMPs is often poor, there have been a number of peptides that demonstrate efficacy including short peptide mimetics [6].

Another antibacterial strategy is to develop agents that sensitize resistant bacteria to approved antibiotics. There have a number of agents reported that sensitize MRSA to beta-lactam (β-lactam) antibiotics. These include small molecules [7-11], peptides [12], peptide mimetics [13], and a human milk protein complex [14].

Accordingly, there remains a need in the art for improved methods and compositions for treating MRSA infections and for sensitizing MRSA to beta-lactam antibiotics.

BRIEF SUMMARY

The present invention provides a synbody that has direct antibiotic activity against methicillin-resistant *Staphylococcus aureus* (MRSA). The synbody is bactericidal against multiple strains of MRSA and likely targets the cell membrane. The synbody also can be used in conjugation with currently approved β-lactam antibiotics, such as oxacillin, to treat MRSA infections, which are normally resistant to β-lactam treatment. This molecule can function as the starting scaffold for medicinal chemistry optimization of activity and pharmacokinetics for future clinical development.

In a first aspect, provided herein is a compound represented by the general formula (I):

where R is R1 or R2, wherein R1 is CSGKRYLQKGK-GALRGLYIF (SEQ ID NO:1), and R2 is [Ac]-RWRRHkH-FkRPHRkHkRGSC-[NH₂].

In another aspect, provided herein is a compound represented by the general formula (II):

where R1 is CSGKRYLQKGKGALRGLYIF (SEQ ID NO:1), and R2 is [Ac]-RWRRHkHFkRPHRkHkRGSC-[NH₂].

In another aspect, provided herein is a pharmaceutical composition comprising the compound in an in an effective amount for reducing or inhibiting growth of methicillin-resistant *Staphylococcus aureus* (MRSA), and a pharmaceutically acceptable carrier. The compound can be present at an effective concentration to reduce the amount of microbial organisms which result in MRSA infection. The microbial organisms can be selected from the group consisting of Methicillin-resistant *Staphylococcus aureus, Staphylococcus aureus, Enterococcus faecalis, Clostridium difficile, Staphylococcus epidermidis*, and a combination thereof In another aspect, provided herein is a pharmaceutical composition useful for the treatment of diseases and infections caused by methicillin-resistant staphylococci, where the composition comprises the compound and at least one beta-lactam antibiotic, each in amounts that act synergistically together to effectively treat said diseases and infections. The at least one beta-lactam antibiotic is selected from the group consisting of oxacillin, amoxicillin, and nafcillin.

In yet another aspect, this disclosure provides a method of treating a MRSA infection, comprising contacting one or more cells infected with MRSA to an effective amount of a compound or a pharmaceutical composition described herein. The pharmaceutical composition can further comprise at least one beta-lactam antibiotic selected from the group consisting of oxacillin, amoxicillin, and nafcillin in an amount that acts synergistically with the compound to effectively treat the MRSA infection.

In another aspect, this disclosure provides a method of reducing or inhibiting the growth of MRSA in a subject, comprising contacting one or more cells infected with MRSA to an effective amount of a compound or a pharmaceutical composition described herein, where said administrating is effective to reduce or inhibit growth of said MRSA. The pharmaceutical composition can further comprise at least one beta-lactam antibiotic selected from the group consisting of oxacillin, amoxicillin, and nafcillin in an amount that acts synergistically with the compound to effectively reduce or inhibit the growth of MRSA in the subject.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description.

DETAILED DESCRIPTION

Definitions

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

As used herein, the singular forms "a", "an" and "the" include plural referents unless the context clearly dictates otherwise. "And" as used herein is interchangeably used with "or" unless expressly stated otherwise. It is also to be noted that the terms "comprising", "including", and "having" can be used interchangeably.

As used herein, the amino acid residues are abbreviated as follows: alanine (Ala; A), asparagine (Asn; N), aspartic acid (Asp; D), arginine (Arg, R), cysteine (Cys; C), glutamic acid (Glu; E), glutamine (Gln; Q), glycine (Gly; G), histidine (His; H), isoleucine (Ile; I), leucine (Leu; L) lysine (Lys; K) methionine (Met M), phenylalanine (Phe; F), proline (Pro; P), serine (Ser S), threonine (Thr; T), tryptophan (Trp; W), tryosine (Tyr; Y), and valine (Val; V). In some cases, lower case letters are used to represent a D-isomer variant of an amino acid. For example, r=D-variant of R (Arg).

All embodiments within and between different aspects of the invention can be combined unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The methods and compositions described herein are based at least in part on the inventors' development of a peptide discovery system and discovery of a bivalent peptide, called a synbody having antimicrobial activity. As demonstrated in the examples that follow, the synbodies provided herein are advantageous over antimicrobial peptides (AMPs) in that the synbodies have robust in vivo antimicrobial activity against multiple MRSA strains while also sensitizing MRSA strains to β-lactam antibiotics.

Accordingly, provided herein are polypeptides and compositions having antimicrobial activity against multiple strains of methicillin resistant *Staphylococcus aureus* (MRSA), and capable of restoring sensitivity of MRSA strains to the effects of beta-lactam (β-lactam) antibiotics. As used herein, the term "beta-lactam antibiotic" or (β-lactam antibiotic) refers to any antibiotic agent that contains a chemical structure that includes a three-carbon, one-nitrogen cyclic amine structure known as the beta-lactam ring. Beta-lactam antibiotics include, without limitation, penicillins (e.g., ampicillin, oxacillin), penems (e.g., imipenem and meropenem), cephalosporins (e.g., cephalexin, cefaclor), monobactams (e.g., aztreonam), and carbapenems (e.g., loracarbef).

In one aspect, provided herein is a synthetic binding molecule or "synbody" comprising peptides conjugated to a peptide scaffold using maleimide thiol conjugation. The terms "synbody" and "synthetic antibody" are used interchangeably in this document and refer to a synthetic binding molecule having antimicrobial activity or capable of inhibiting a biological activity associated with bacterial growth or survival.

Figures 1A, 1B:
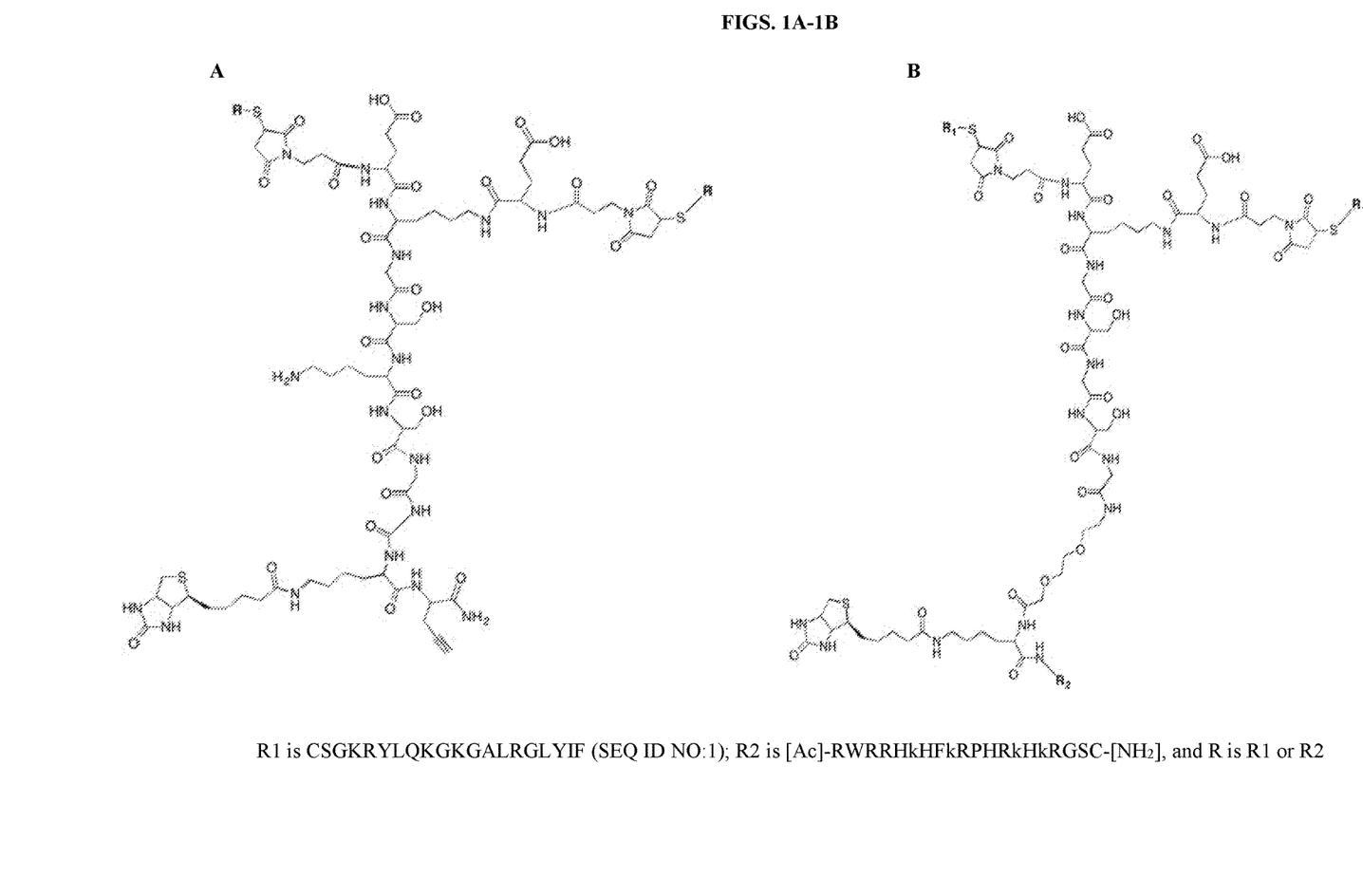
FIGS. 1A-1B provide exemplary structures of chemical appropriate for use in the compositions provided herein. (A) Chemical structure of ASU015, which is a derivative of ASU014, where R1=CSGKRYLQKGKGALRGLYIF (SEQ ID NO:1), and R2=[Ac]-RWRRHkHFkRPHRkHkRGSC-[NH$_2$]. (B) Chemical structure of ASU014, where R1=CSGKRYLQKGKGALRGLYIF (SEQ ID NO:1) and R2=[Ac]-RWRRHkHFkRPHRKRGSC-[NH$_2$]. Lower case amino acids represent D-isomer variants of the amino acid. For example, r=D-variant of R (Arg).

In some cases, the synbody comprises peptides R1 and R2 conjugated a bis-maleimide peptide scaffold. In exemplary embodiments, the synbody comprises peptides R1 and R2, conjugated a bis-maleimide peptide scaffold, where the synbody has the chemical formula shown in FIG. 1A and where R1 is CSGKRYLQKGKGALRGLYIF (SEQ ID NO:1), and R2 is [Ac]-RWRRHkHFkHFkRPHRkHkRGSC-[NH$_2$]. As described in the Examples that follow, a synbody having the chemical structure shown in FIG. 1A (identified throughout as ASU014) has a Minimum Inhibitory Concentration (MIC) of 50 μM for methicillin-sensitive *S. aureus* (MSSA), is non-toxic to human cells in vitro, and does not generate acute toxicity in vivo in animal studies.

In other embodiments, the synbody further includes a functional element such as an antibiotic, an imaging agent, or a cell-penetrating peptide such as HIV-TAT peptide. In other cases, the synbody includes an agent capable of intracellular targeting of MRSA. See Lehar et al., *Nature*, doi:10.1038/nature16057.

As used herein, the term "antimicrobial activity" refers to the capacity of a chemical compound or therapeutic agent to effectively reduce bacterial infection in a subject or to reduce or inhibit growth of a bacterial organism in culture. In an exemplary embodiment, the synbodies provided herein inhibit the growth of multiple strains of MRSA having MICs ranging from about 25 μM to about 100 μM.

In another aspect, provided herein are methods for reducing or preventing growth of a MRSA strain. In treating a MRSA infection, one would contact an infected subject with a synbody as provided herein. This can be achieved by contacting the infected subject or the infecting microorganisms with the synbody by administering to the subject a therapeutically effective amount of a pharmaceutical composition comprising a synbody having antibacterial activity against one or more MRSA strains. A pharmaceutical composition can comprise an effective amount of a synbody described herein and a pharmaceutically acceptable carrier. The terms "pharmaceutically acceptable" and "pharmacologically acceptable" refer to compositions that do not produce an adverse, allergic or other untoward reaction when administered to an animal, or a human as appropriate. As used herein, the term "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

As used herein, the term "effective amount" refers to those amounts effective to reproducibly reduce the growth of a bacterial strain, in comparison to their normal levels (i.e., level of growth in the absence of the synbody). Significant decrease in growth, e.g., as measured using a growth assay, of at least about 30%-40%, and most preferably, by decreases of at least about 50%. with higher values of course being possible.

Pharmaceutical compositions comprising an antibacterial synbody described herein can be formulated for administration/use via any suitable route, including but not limited to orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques a intraperitoneally. In preferred embodiments, the compositions are formulated for administration/use as a topical cream, a suspension, an oral formulation, or an intravenous formulation. In some cases, the antibacterial polypeptides provided herein may be the sole active agent in the pharmaceutical composition. In other cases, the pharmaceutical composition may further comprise one or more other active agents or carrier moieties suitable for an intended use. For example, a pharmaceutical composition comprising an ASU014 synbody may also comprise one or more β-lactam antibiotics to which MRSA strains typically have resistance. Such b-lactam antibiotics include, without limitation, oxacillin, amoxicillin, and nafcillin. In other cases, a pharmaceutical composition comprising an ASU014 synbody can further comprise another antimicrobial agent such as a sulfonamide, a quinolone, a penicillin, a cephalosporin, an aminoglycoside, or a tetracycline.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired. Some variation in dosage will necessarily occur depending on the condition of the subject being treated. Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular therapeutic substance. The person responsible for administration will, in any event, determine the appropriate dose for the individual subject. Moreover, for human administration, preparations should meet sterility and general safety and purity standards.

It is expected that regional delivery of a pharmaceutical composition provided herein to patients having a MRSA infection will be a very efficient method for delivering a therapeutically effective composition to counteract the clinical disease. In some cases, the composition can be directed or applied to a particular, affected region of the subject's body. For subjects having extensive infections, systemic delivery of the pharmaceutical composition may be appropriate.

Peptides identified according to the methods described herein are ideally non-toxic to human cells and do not generate an immune response or acute toxicity in vivo.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments. All technical publications, patents and published patent applications cited herein are hereby incorporated by reference in their entirety for all purposes.

EXAMPLES

The invention will be more fully understood upon consideration of the following non-limiting Example. The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

Example 1

ASU014 Acts Synergistically with β-lactam Antibiotics against Methicillin Resistant *Staphylococcus Aureus* (MRSA)

Figures 2A, 2B, 2C:
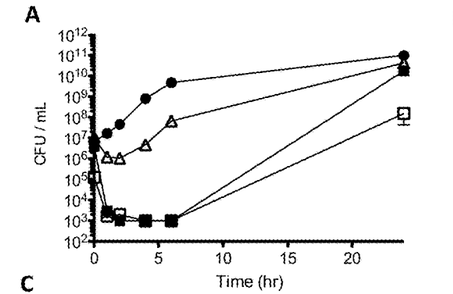
FIGS. 2A-2C demonstrate the effects of treatment with ASU014. (A) Time-kill kinetics of ASU014 versus USA300-HI1168 (circles). The synbody was added at 2× MIC (open squares), 1× MIC (filled squares), or 0.5× MIC (triangles) and incubated for the indicated times. (B) Change in membrane potential of ASU014 treated USA300-HI-168 as measured by DiSc$_3$(5) fluorescence. ASU014 at 1× MIC (circles), 0.25% sodium deoxycholate (triangles), or a negative control synbody (squares) were added at t=5 minutes. (C) Change in membrane permeability of ASU014 treated USA300-HI168. ASU014 at 1× MIC (circles), 0.25% sodium deoxycholate (triangles), or a negative control synbody (squares) were added at t=20 minutes.

Experiments were conducted to assay ASU014's potential as a single agent against MRSA and as a potential MRSA sensitizer. First, we measured ASU014's antibacterial activity against a panel of MRSA isolates and several Gram-negative pathogens. The data revealed that the ASU014 synbody was antibacterial against multiple strains of MRSA that are highly resistant to β-lactam antibiotics such as oxacillin (Table 1). We also observed a collapse in membrane potential immediately upon addition of ASU014 (FIG. 2B). Ten minutes post-exposure, cell permeability increased, suggesting that ASU014 permeabilizes the cell membrane (FIG. 2C). ASU014 having a MIC of 50 μM for MRSA had no detectable inhibitory effect against the Gram-negative bacteria after overnight incubation (Table 1).

TABLE 1

MIC against a panel of Gram-positive and Gram-negative bacteria.

| Species | Strain/reference | ASU014 MIC (μM) | Oxa MIC (μg/mL) | Cipro MIC (μg/mL) |
|---|---|---|---|---|
| MSSA | Domenyuk et al., *PLoS ONE* 8(1): e54162 (2013) | 50 | <0.25 | 0.25 |
| MRSA (USA100) | BEI: HFH-30123 | 50 | >128 | >4 |
| MRSA (USA300) | BEI: FOO3/HI168 | 50 | 32 | 0.5 |
| MRSA (USA300-LAC) | | 25 | 64 | |
| MRSA (USA400) | BEI: HFH-30364 | 50 | 8 | 0.5 |
| MRSA (USA500) | BEI: HFH-30522 | >50 | 8 | >4 |
| S. epidermidis | ATCC-29886 | <6.25 | | |
| P. aeruginosa | PAO1 | n.i. | | 0.5 |
| E. coli O157:H7 | BEI: BAA-1883 | n.i. | | <1 |
| B. thailandensis | ATCC 700388 | n.i. | | | n.i. = no inhibition

Figure 3A:
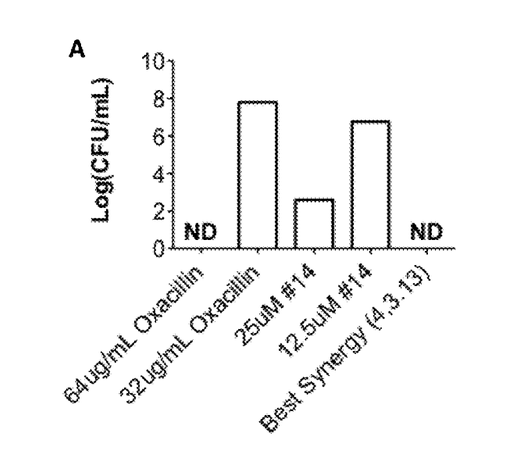
FIGS. 3A-3B demonstrate in vitro synergy of ASU014 with oxacillin. (A) Activity of ASU014 when tested in combination with oxacillin for USA300-LAC. (B) Activity of ASU014 when tested in combination with oxacillin for USA100 strain.
Figure 3B:
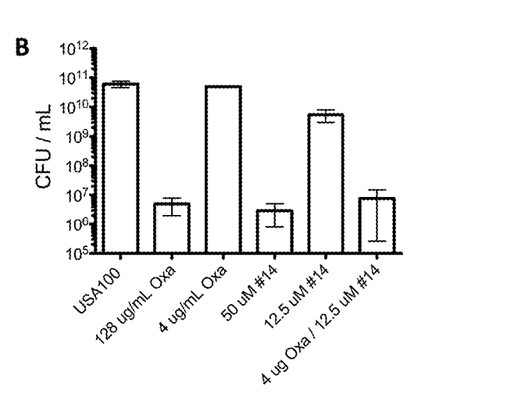

The in vivo effects of ASU014 treatment, either alone or in combination with oxacillin, were assayed using an in vivo pouch model of MRSA infection [16, 17]. It was observed that a sub-MIC concentration of ASU014 and a sub-MIC concentration of oxacillin reduced growth of MRSA-USA100 (FIG. 3A) and MRSA-USA300 (FIG. 3B). The fractional inhibitory concentration (FIC) value of MRSA USA300-LAC was 0.25. The FIC of MRSA USA100 was 0.30.

To confirm that these in vivo effects were not unique to oxacillin, we tested combinations of ASU014 with amoxicillin and nafcillin. Our results revealed that ASU014 has synergistic activity with both nafcillin (FIC=0.31) and amoxicillin (FIC=0.38) despite the high MIC of amoxicillin (>256 ug/mL) for this MRSA strain.

TABLE 2

Synergy with β-lactam Antibiotics.

| | | Antibiotic MIC (μg/mL)/(FIC) | | | |
|---|---|---|---|---|---|
| Antibiotic and *S. aureus* strain | ASU014 MIC (μM) | Antibiotic Only | +⅛ MIC (ASU014) | +¼ MIC (ASU014) | +½ MIC (ASU014) |
| Oxacillin | | | | | |
| USA100 | 50 | 128 | 64 (0.63) | 8 (0.31) | 4 (0.53) |
| USA300-LAC | 25 | 64 | 8 (0.25) | 4 (0.31) | 4 (0.56) |
| USA300-HI168 | 50 | 2 | 0.5 (0.38) | 0.125 (0.31) | 0.063 (0.53) |
| MSSA UAB637 | 100 | 0.125 | 0.125 | 0.125 | 0.125 |
| Amoxicillin | | | | | |
| USA100 | 50 | >256 | >256 | 32 (0.38) | 4 (0.52) |
| Nafcillin | | | | | |
| USA100 | 50 | 32 | 8 (0.38) | 2 (0.31) | 2 (0.56) |
| Ciprofloxacin | | | | | |
| USA100 | 50 | >32 | >32 | >32 | >32 |

TABLE 2-continued

Synergy with β-lactam Antibiotics.

| Antibiotic and S. aureus strain | ASU014 MIC (μM) | Antibiotic Only | Antibiotic MIC (μg/mL)/(FIC) | | |
|---|---|---|---|---|---|
| | | | +⅛ MIC (ASU014) | +¼ MIC (ASU014) | +½ MIC (ASU014) |
| Streptomycin | | | | | |
| USA300-HI168 | 50 | 4 | 4 | 2 (0.75) | 0.5 (0.63) |

Figure 4A:
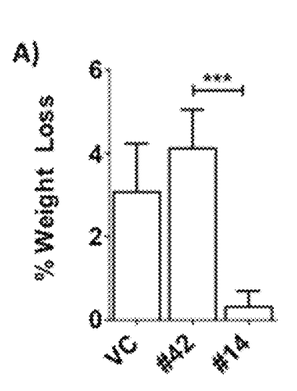
FIGS. 4A-4C demonstrate activity of ASU014 against MRSA in an in vivo pouch model. (A) Activity against MRSA in an in vivo pouch model. The weight loss of mice infected with 3×10$^7$ CFU/mL of USA300-Lac treated simultaneously with either vehicle control (VC), (42), or 4× MIC ASU014. (B) Bacterial counts in the pouch show a significant reduction in bacterial load with ASU014 treatment. *$p<0.05$. $p<0.01$ *$p<0.001$. (C) Bacterial counts disseminated to the kidneys show a significant reduction in bacterial load with ASU014 treatment. *$p<0.05$. $p<0.01$ *$p<0.001$.
Figures 4A, 4B, 4C:
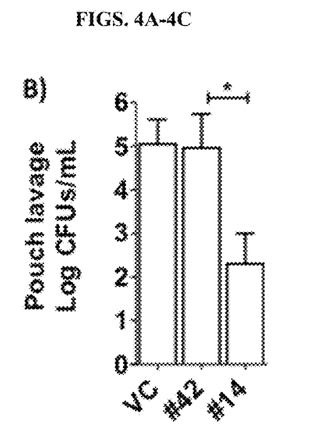
Figure 4C:
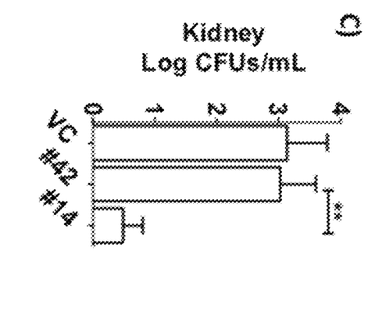

We tested ASU014, a negative control synbody, and a vehicle control for in vivo activity in an air pouch model of MRSA infection [16, 17]. In this model, mice (n=8 per group) were challenged with either 107 CFU/mL of USA300-LAC plus vehicle control, USA300-LAC plus 100 μM (ASU014), or USA300-LAC plus 100 μM (ASU042). The following day, mice were weighed and bacterial counts enumerated in the pouch and those that had disseminated to the kidneys. Vehicle treated mice lost ~3% body weight, negative control treated mice lost ~5% body weight while (ASU014) treated mice lost less than 1% weight (p<0.01) (FIG. 4A). Mice treated with (ASU014) had large reductions in bacterial counts in both the pouch (p<0.05) and kidneys (p<0.01) (FIGS. 4B-C). These results demonstrate that ASU014 functions in an in vivo infection model.

We tested synergy with oxacillin in the MRSA air pouch model. In this assay, mice were challenged with 107 CFU/mL of USA300-LAC plus vehicle control, USA300-LAC plus 12.5 μM ASU014, USA300-LAC plus 64 μg/mL oxacillin or USA300-LAC and 12.5 μM ASU014 plus 64 μg/mL oxacillin. The following day, mice were assigned a clinical score [17] as a measure of morbidity, weighed and bacterial counts enumerated in the pouch and kidneys.

Figure 5A:
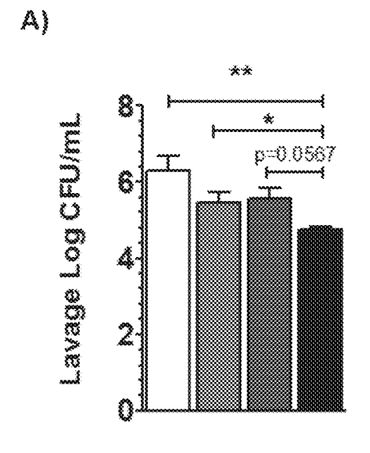
FIGS. 5A-5D demonstrate synergy with oxacillin against MRSA in an in vivo pouch model. (A) Bacterial counts disseminated to the kidneys after treatment with either vehicle control (first column from the left), 12.5 µM ASU014 (second column from the left), 64 µg/mL oxacillin (third column from the left) or 12.5 µM ASU014 plus 64 µg/mL oxacillin (fourth column from the left). (B) Synergy with oxacillin against MRSA in an in vivo pouch model. Bacterial counts disseminated to the kidneys after treatment with either vehicle control (first column from the left), 12.5 µM ASU014 (second column from the left), 64 µg/mL oxacillin (third column from the left) or 12.5 µM ASU014 plus 64 µg/mL oxacillin (fourth column from the left). (C) The weight loss of mice show a significant reduction in bacterial burden, weight loss, and clinical score when treated with the combination of ASU014 and oxacillin. *$p<0.05$. $p<0.01$ *$p<0.001$. (D) The clinical score of mice show a significant reduction in bacterial burden, weight loss, and clinical score when treated with the combination of ASU014 and oxacillin. *$p<0.05$. $p<0.01$ *$p<0.001$.
Figure 5B:
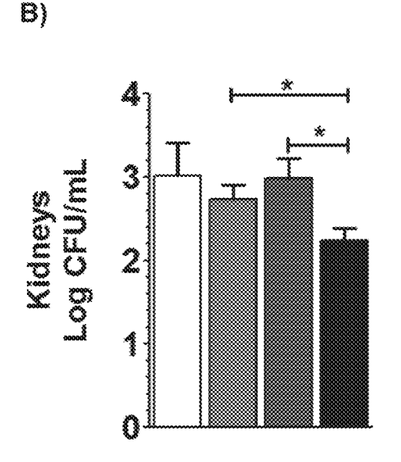
Figure 5C:
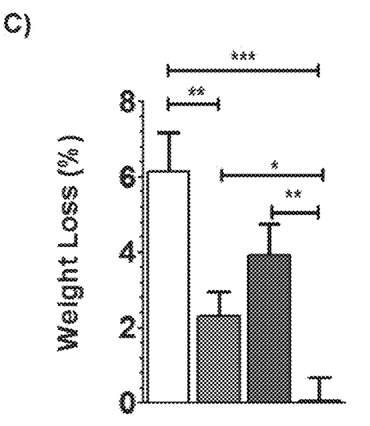
Figure 5D:
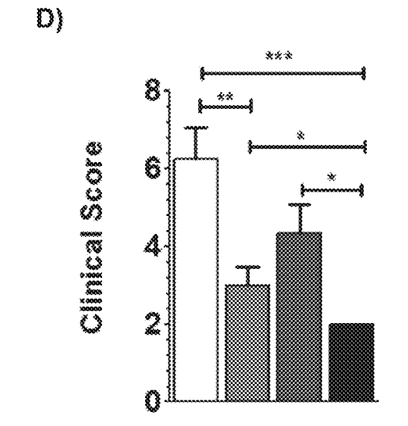

The combination of ASU014 and oxacillin significantly reduced the bacterial burden in the pouch compared to both the vehicle control and either single treatment (FIG. 5A). The combination treatment reduced dissemination to the kidneys more than either single treatment (FIG. 5B). The combination treatment provided the greatest reduction in clinical symptoms of infection (FIGS. 5C-D) suggesting that in addition to a direct antibacterial effect, the combination treatment effects USA300-LAC virulence.

Example 2
Preparing a Pharmaceutical Composition Comprising ASU014 Synbodies for Use against MRSA Synbodies having direct antibiotic activity against methicillin resistant *Staphylococcus aureus* (MRSA) are prepared by adding 1.1 molar equivalents of peptide R1 and 1.1 molar equivalents of peptide R2 to a bis-maleimide peptide scaffold in aqueous buffer. After overnight incubation, the synbody ASU014 is purified by HPLC and lyophilized prior to use. The lyophilized synbody is dissolved in aqueous buffer and then used as other antibiotics are used. For in vivo use, the synbody is delivered by infusion, intravenous injection, or intraperitoneal injection.

REFERENCES

1. WHO (2014) Antimicrobial resistance: global report on surveillance, 2014.
2. CDC (2013) Antibiotic resistance threats in the United States, 2013.
3. Boucher H W et al. (2013) Clinical Infectious Diseases 56: 1685-1694.
4. Lewis K (2013). Nat Rev Drug Discov 12: 371-387.
5. Mercer D K (2013) Future Medicinal Chemistry 5: 315-337.
6. Sarig H et al. (2010) The FASEB Journal 24: 1904-1913.
7. Farha Maya A (2013) Chemistry & Biology 20: 1168-1178.
8. Podoll J D et al. (2013) Proceedings of the National Academy of Sciences 110: 15573-15578.
9. Mann P A et al. (2013) ACS Chemical Biology 8: 2442-2451.
10. Wang H et al. (2013) Chemistry & Biology 20: 272-284.
11. Lu X et al. (2013) PLoS One 8: e68053.
12. Li Z et al. (2014) PLoS One 9: e97539.
13. Kaneti G (2013) The FASEB Journal 27: 4834-4843.
14. Marks L R (2013) PLoS One 8: e63158.
15. Domenyuk et al. (2013) PLoS One 8:e54162.
16. Sully E K, et al. (2014) PLoS Pathog 10: e1004174.
17. Hall P R, et al. (2013) PLoS Pathog 9: e1003166.

We claim:

1. A compound represented by a general formula selected from the group consisting of (I) and (II), wherein formula (I) is wherein formula (II) is and wherein R1 is CSGKRYLQKGKGALRGLYIF (SEQ ID NO:1), R2 is [Ac]-RWRRHkHFkRPHRkHkRGSC-[NH$_2$], and R is either R1 or R2.

2. A pharmaceutical composition comprising the compound of claim 1 in an effective amount for reducing or inhibiting growth of methicillin-resistant *Staphylococcus aureus* (MRSA), and a pharmaceutically acceptable carrier.

3. The pharmaceutical composition of claim 2, wherein the compound is present at an effective concentration to reduce the amount of microbial organisms which result in MRSA infection.

4. The pharmaceutical composition of claim 3, wherein the microbial organisms are selected from the group consisting of Methicillin-resistant *Staphylococcus aureus, Staphylococcus aureus, Enterococcus faecalis, Clostridium difficile*, and *Staphylococcus epidermidis*, or a combination thereof.

5. A pharmaceutical composition useful for the treatment of diseases and infections caused by methicillin-resistant staphylococci, wherein the composition comprises the compound of claim 1 and at least one beta-lactam antibiotic, each in amounts that act synergistically together to effectively treat said diseases and infections.

6. The pharmaceutical composition of claim 5, wherein the at least one beta-lactam antibiotic is selected from the group consisting of oxacillin, amoxicillin, and nafcillin.

7. A method of treating a MRSA infection, comprising contacting one or more cells infected with MRSA with an effective amount of the compound of claim 1 or the pharmaceutical composition of claim 2.

8. The method of claim 7, wherein the compound is in a pharmaceutical composition which further comprises at least one beta-lactam antibiotic selected from the group consisting of oxacillin, amoxicillin, and nafcillin in an amount that acts synergistically with the compound to effectively treat the MRSA infection.

9. A method for reducing or inhibiting the growth of MRSA in a subject, the method comprising administering to the subject an effective amount of the pharmaceutical composition of claim 2, wherein said administrating is effective to reduce or inhibit the growth of said MRSA.

10. The method of claim 9, wherein the pharmaceutical composition further comprises at least one beta-lactam antibiotic selected from the group consisting of oxacillin, amoxicillin, and nafcillin in an amount that acts synergistically with the compound to effectively reduce or inhibit the growth of MRSA in the subject.

* * * * *

UNITED STATES PATENT AND TRADEMARK OFFICE
CERTIFICATE OF CORRECTION

PATENT NO. : 10,125,167 B2
APPLICATION NO. : 15/368178
DATED : November 13, 2018
INVENTOR(S) : Chris Diehnelt et al.

Page 1 of 1

It is certified that error appears in the above-identified patent and that said Letters Patent is hereby corrected as shown below:

In the Specification

Column 7, Line 21, "RWRRHkHFkHFRPHRkHkRGSC" should be --RWRRHkHFkRPHRkHkRGSC--.

Signed and Sealed this
Eighth Day of January, 2019

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: synthetic

<400> SEQUENCE: 1

Cys Ser Gly Lys Arg Tyr Leu Gln Lys Gly Lys Gly Ala Leu Arg Gly
1               5                   10                  15

Leu Tyr Ile Phe
            20
```